(12) United States Patent
Eisinger et al.

(10) Patent No.: US 11,547,438 B2
(45) Date of Patent: Jan. 10, 2023

(54) TIP PROTECTOR FOR ENSURING TROCAR INSERTION

(71) Applicant: Covidien LP, Mansfield, MA (US)

(72) Inventors: Joseph Eisinger, Northford, CT (US); David E. Valentine, Hamden, CT (US); Patrick Mozdzierz, Glastonbury, CT (US)

(73) Assignee: COVIDIEN LP, Mansfield, MA (US)

( * ) Notice: Subject to any disclaimer, the term of this patent is extended or adjusted under 35 U.S.C. 154(b) by 356 days.

(21) Appl. No.: 16/799,172

(22) Filed: Feb. 24, 2020

(65) Prior Publication Data

US 2021/0259727 A1 Aug. 26, 2021

(51) Int. Cl.
*A61B 17/34* (2006.01)
*A61B 90/00* (2016.01)
*A61B 17/115* (2006.01)
*A61B 17/00* (2006.01)

(52) U.S. Cl.
CPC ...... *A61B 17/3417* (2013.01); *A61B 17/3496* (2013.01); *A61B 90/08* (2016.02); *A61B 17/1155* (2013.01); *A61B 2017/0046* (2013.01); *A61B 2017/00486* (2013.01); *A61B 2017/347* (2013.01); *A61B 2090/0813* (2016.02)

(58) Field of Classification Search
CPC ............................ A61B 90/08; A61B 17/3496
See application file for complete search history.

(56) References Cited

U.S. PATENT DOCUMENTS

| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |

(Continued)

FOREIGN PATENT DOCUMENTS

| CA | 908529 A | 8/1972 |
| CA | 2805365 A1 | 8/2013 |

(Continued)

OTHER PUBLICATIONS

European Search Report dated Jun. 22, 2021, corresponding to counterpart European Application No. 21159083.1; 7 pages.

*Primary Examiner* — Nathaniel C Chukwurah
(74) *Attorney, Agent, or Firm* — Carter, DeLuca & Farrell, LLP (57) ABSTRACT

A device for loading a trocar assembly with an adapter assembly of a surgical stapling instrument and a method of confirming that the trocar assembly is properly secured to the adapter assembly are provided. The device includes a base member and an engagement arm secured to the base member. The base member defines a longitudinal passage for receiving a trocar assembly and includes a proximal end surface. The engagement arm is configured to releasably secure a trocar assembly within the base member. The engagement arm includes a proximal end surface. The proximal end surface of the base member is configured to engage a distal end surface of a trocar housing of the trocar assembly when the trocar assembly is not properly secured within the adapter assembly.

20 Claims, 7 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |

(56) References Cited

U.S. PATENT DOCUMENTS

| | | |
|---|---|---|
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,023,014 B2 | 5/2015 | Chowaniec et al. |
| 9,055,943 B2 | 6/2015 | Zemlok et al. |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |

(56) References Cited

U.S. PATENT DOCUMENTS

| | | |
|---|---|---|
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0106406 A1 | 4/2016 | Cabrera et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0086879 A1 | 3/2017 | Williams |
| 2017/0340348 A1* | 11/2017 | Cabrera ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3593736 A2 | 1/2020 |
| EP | 3701885 A2 | 9/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

TIP PROTECTOR FOR ENSURING TROCAR INSERTION

FIELD

The present disclosure relates to circular stapling instruments. More particularly, the present disclosure relates to devices and methods for facilitating insertion and alignment of trocar assemblies within adapter assemblies for circular stapling instruments.

BACKGROUND

Surgical instruments for applying staples, clips, or other fasteners to tissue are well known. Typically, endoscopic stapling instruments include an actuation unit, e.g., a handle assembly for actuating the instrument, an elongate shaft for accessing a body cavity, and a tool assembly disposed at a distal end of the elongate shaft.

Adapter assemblies used with a circular stapling tool assembly typically include a trocar assembly for selectively positioning an anvil assembly relative to a cartridge assembly. To facilitate sterilization and reuse of the adapter assemblies, many of the trocar assemblies are removable. Subsequent to cleaning and sterilizing, and prior to reuse, the adapter assemblies need to be reassembled by hospital staff or other personnel. Ensuring that the adapter assembly is properly reassembled is important for functionality and patient safety of the circular stapling instruments.

SUMMARY

According to an aspect of the disclosure, a trocar loading device for loading a trocar assembly within an adapter assembly is provided. The trocar loading device includes a base member defining a longitudinal passage for receiving a trocar assembly and including a proximal end surface; and an engagement arm secured to the base member and configured to releasably secure a trocar assembly within the base member, the engagement arm including a proximal end surface. The proximal end surface of the base member is configured to engage a distal end surface of a trocar housing of the trocar assembly when the trocar assembly is not properly secured within the adapter assembly.

The proximal end surface of the engagement arm may be configured to engage a distal end surface of a connection member of the adapter assembly when the trocar assembly is properly secured within the adapter assembly.

The base member may include a connector portion configured to be received within the connection member of the adapter assembly.

The base member may include a handle portion configured for operable engagement by a user.

The engagement arm may include an elongate portion, a C-shaped flange portion disposed on a first end of the elongate portion, and a locking portion extending from the flange portion.

The engagement arm may further include a release portion disposed adjacent the C-shaped flange portion and which may be configured for operable engagement by a user.

The engagement arm may be formed from a single piece of material.

The engagement arm may be secured to the base member by the screw.

The base member may include a tapered section to accommodate flexing of the engagement arm.

The locking portion of the engagement arm may include an inclined surface to facilitate receipt of a trocar assembly within the base member.

According to a further aspect of the present disclosure, a method of confirming proper securing of a removable trocar assembly within an adapter assembly is provided. The method includes securing a trocar loading device to the removable trocar assembly; receiving proximal ends of the removable trocar assembly and the trocar loading device within the adapter assembly; and retracting a trocar member of the trocar assembly proximally until a proximal end surface of an engagement arm of the trocar loading device engages a distal end surface of a connection member of the adapter assembly or a proximal end surface of a base member of the trocar loading device engages a distal end surface of a trocar housing of the removable trocar assembly.

The method may further include advancing the trocar member relative to the trocar housing to permit securing of the trocar loading unit to the removable trocar assembly.

The securing of the trocar loading device to the removable trocar assembly may include receiving a locking portion of the engagement arm through a slot in the trocar member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Aspects of the disclosed device and method for ensuring proper engagement of a removable trocar assembly with an adapter assembly will now be described in detail with reference to the drawings in which like reference numerals designate identical or corresponding elements in each of the several views. As is common in the art, the term "proximal" refers to that part or component closer to the user or operator, e.g. surgeon or clinician, while the term "distal" refers to that part or component farther away from the user.

Figure 1:
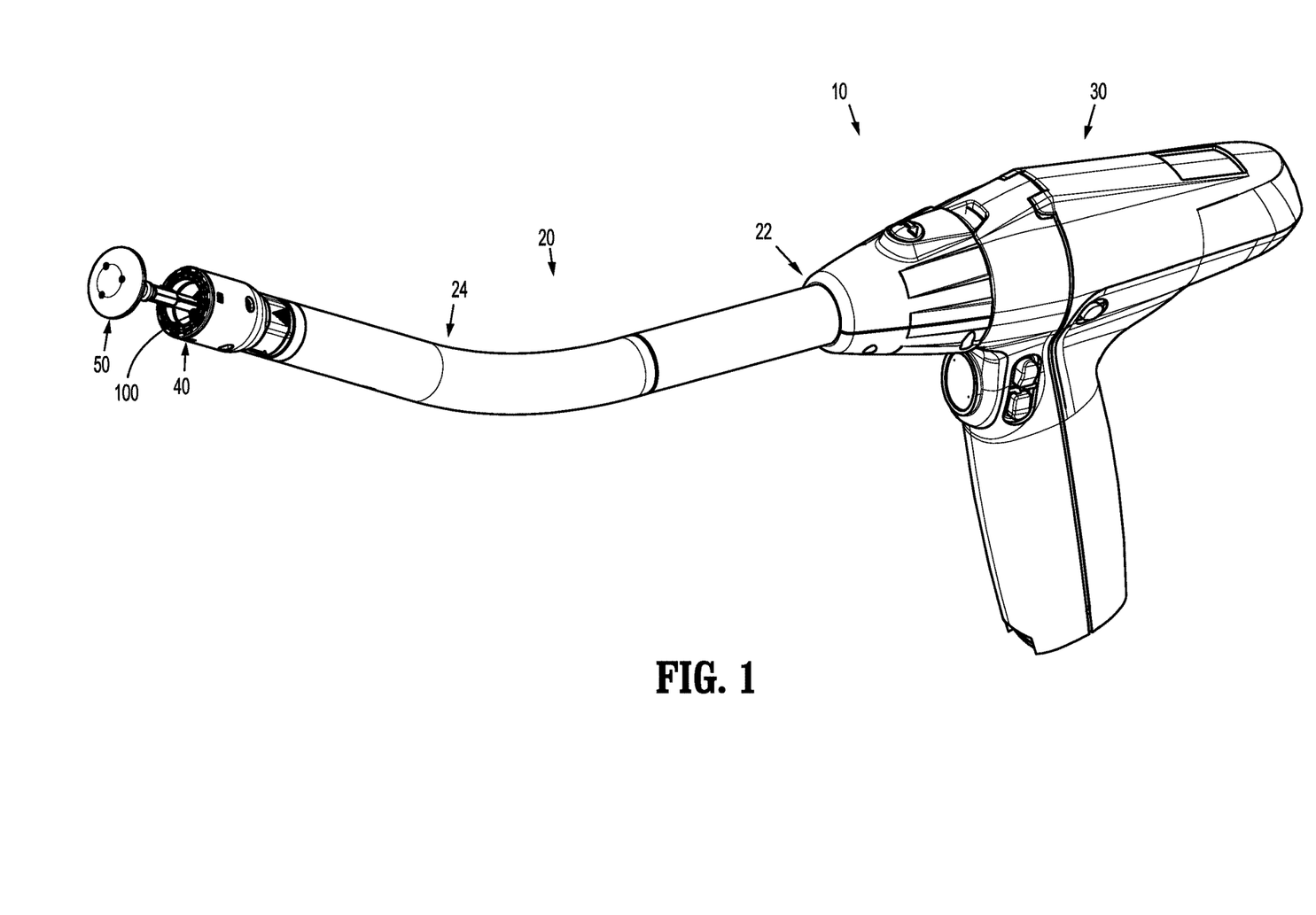
FIG. 1 is a perspective view of a surgical stapling instrument, including an adapter assembly and a removable trocar assembly, suitable for use with a trocar loading device according to an aspect of the disclosure.

FIG. 1 illustrates a surgical stapling instrument 10 including an adapter assembly suitable for use with the loading device and method of the disclosure, shown generally as adapter assembly 20. The surgical stapling instrument 10 further includes a powered handle assembly 30, a loading unit 40, and an anvil assembly 50. Although shown and described with reference to the surgical stapling instrument 10 and the adapter assembly 20, the aspects of the disclosure may be modified for use with surgical stapling instruments having alternative configurations. For a detailed description of exemplary powered surgical stapling instruments, please refer to commonly owned U.S. Pat. No. 9,023,014 ("the '014 patent) and U.S. Pat. No. 9,055,943 ("the '943 patent.

The adapter assembly 20 of the surgical stapling instrument 10 will only be described to the extent necessary to fully disclose the aspects of the present disclosure. For a detailed description of exemplary adapter assemblies, please refer to commonly owned U.S. Pat. App. Pub. Nos. 2016/0106406 ("the '406 publication) and 2017/0086879 ("the '879 publication").

Figure 2:
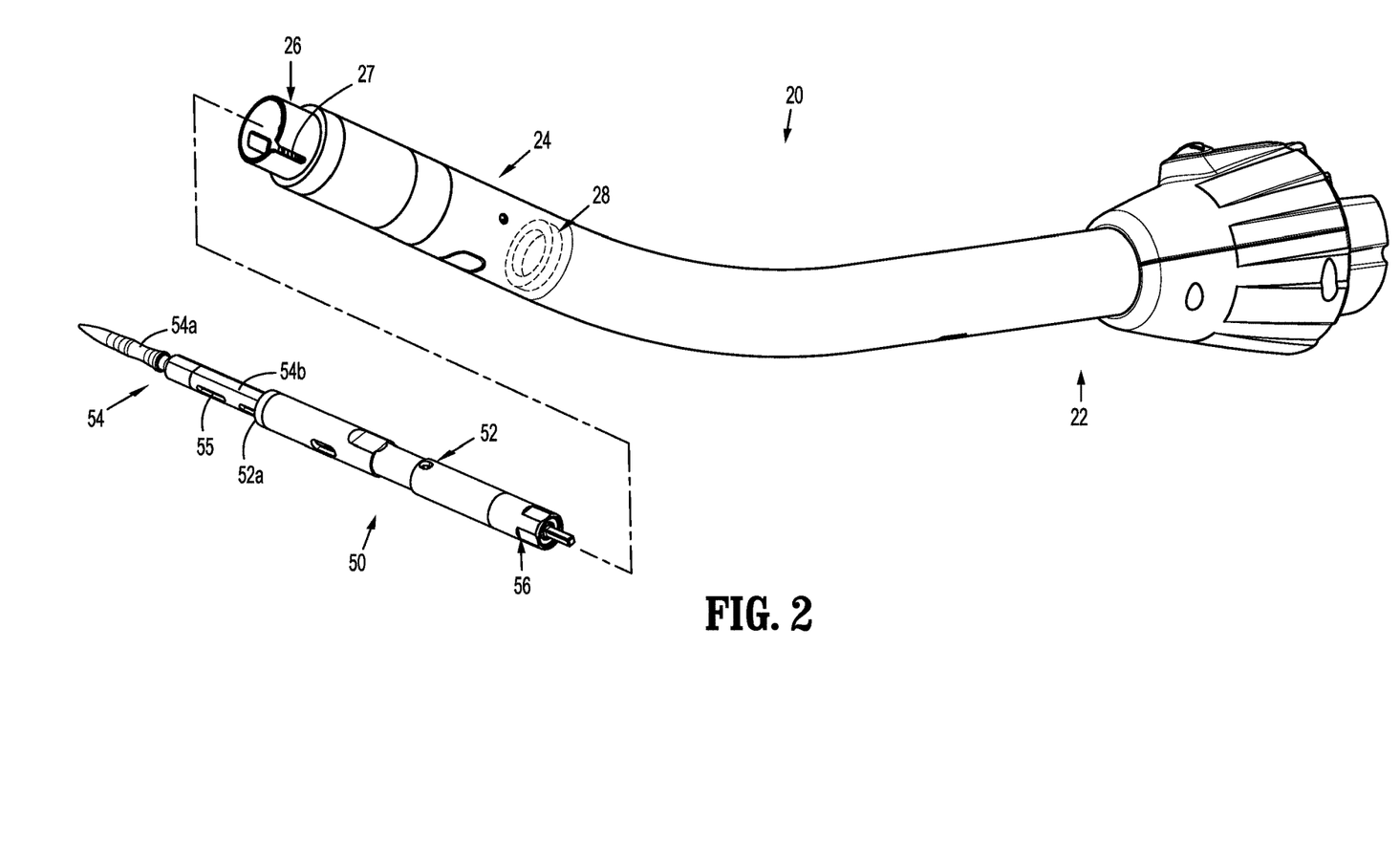
FIG. 2 is a perspective view of the adapter assembly and the removable trocar assembly of the surgical stapling instrument shown in FIG. 1 with removable trocar assembly removed from the adapter assembly.

FIG. 2 illustrates the adapter assembly 20 of the surgical stapling instrument 10, including a proximal portion 22 configured for operable connection to the handle assembly 30 (FIG. 1) and a distal portion 24 configured for operable connection to the loading unit 40 (FIG. 1). Although shown and described as forming an integral unit, it is envisioned that the proximal and distal portions 22, 24 of the adapter assembly 20 may be formed as separate units that are releasably securable to one another. The distal portion 24 of the adapter assembly 20 includes a connection member 26 for releasably connecting the loading unit 40 with the adapter assembly 20. A strain gage assembly 28 (shown in phantom) is disposed within the adapter assembly 20 and operably engages the connection member 26 and a removable trocar assembly 50 to measure strain in the adapter assembly 20 prior to during, and/or subsequent to a stapling procedure.

The removable trocar assembly 50, is releasably securable within the distal portion 24 of the adapter assembly 20. The removable trocar assembly 50 is configured to engage the anvil assembly 50 (FIG. 1) and position the anvil assembly 50 relative to the loading unit 40 (FIG. 1). The removable trocar assembly 50 will only be described to the extent necessary to fully disclose the aspects of the present disclosure. For a detailed description of an exemplary trocar assembly, please refer to the '879 publication.

Figure 5:
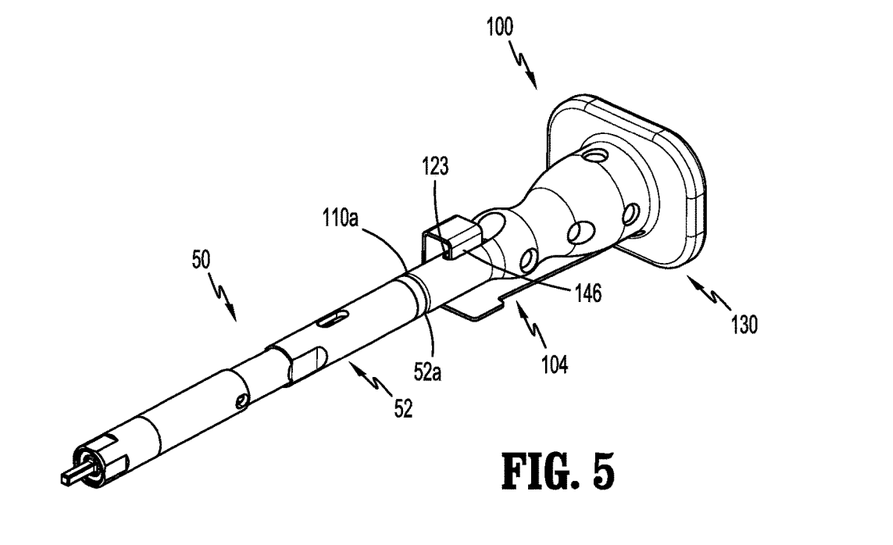
FIG. 5 is a side, perspective view of the removable trocar assembly and the trocar loading device shown in FIG. 4 secured to one another.
Figure 6:
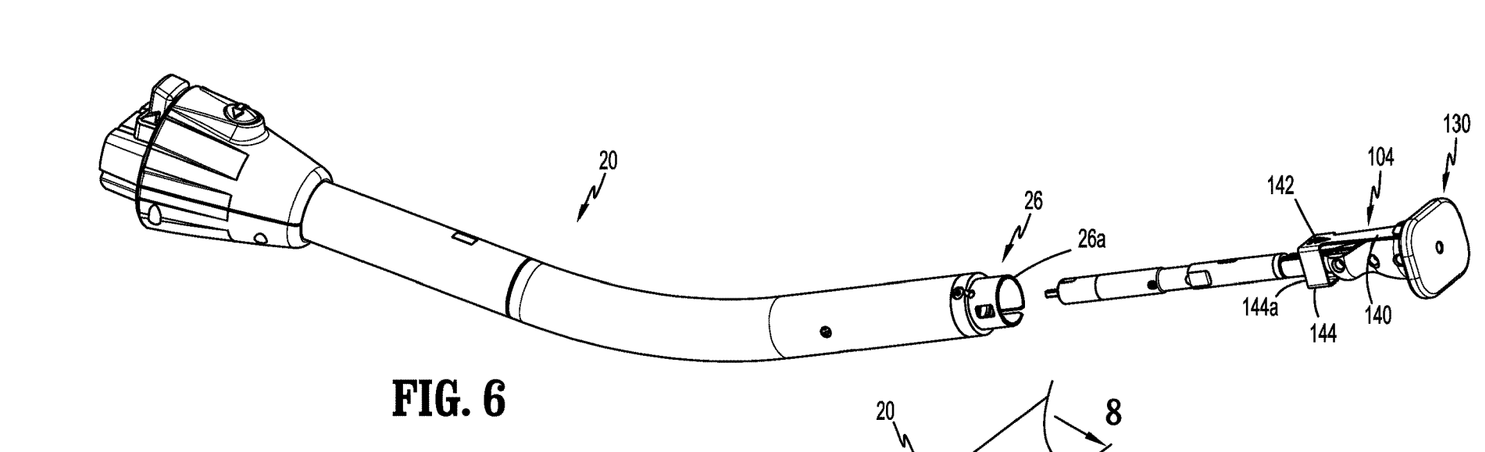
FIG. 6 is a side, perspective view of the adapter assembly shown in FIG. 2 and the removable trocar assembly and the trocar loading device shown in FIG. 5 prior to the removable trocar assembly being received within the adapter assembly.
Figure 7:
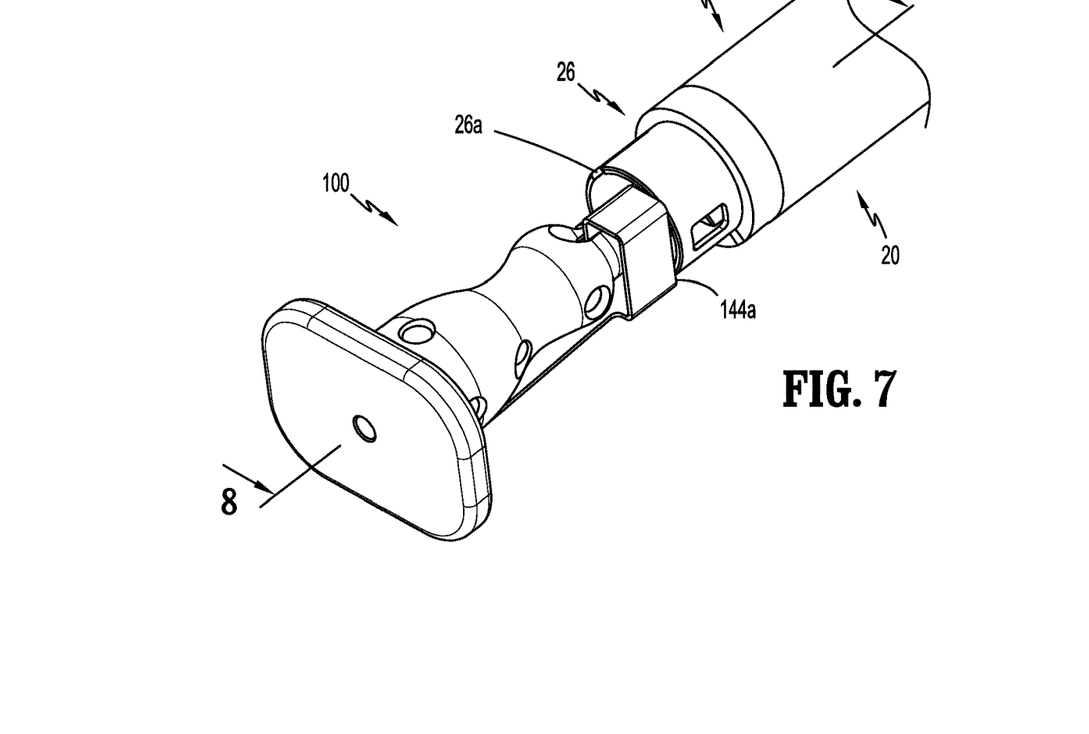
FIG. 7 is an end, perspective view of distal ends of the adapter assembly, removable trocar assembly, and the trocar loading device shown in FIG. 6.

The removable trocar assembly 50 includes a housing 52, a trocar member 54 slidably disposed within the housing 52, and a drive member 56 (FIG. 8) operably received within the trocar member 54 for axially moving the trocar member 54 relative to the housing 52. A tapered distal portion 54a of the trocar member 54 is configured to releasably connect the anvil assembly 50 (FIG. 1) of the surgical stapling instrument 10 (FIG. 1) with the adapter assembly 20. A body portion 54b of the trocar member 54 defines an engagement slot 55. As will be described in further detail below, the engagement slot 55 receives a locking portion 146 (FIG. 5) of an engagement arm 104 of a trocar loading device 100.

Figure 3:
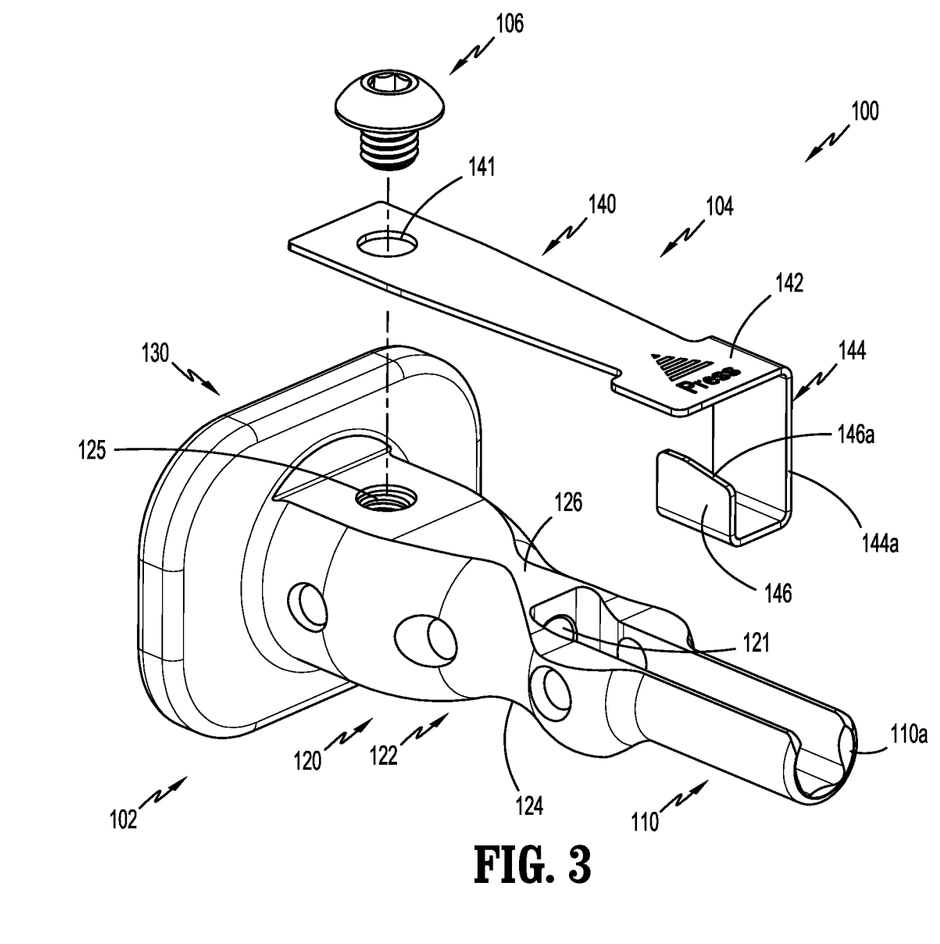
FIG. 3 is a side, perspective view of a trocar loading device according to an aspect of the disclosure, with components separated.
Figure 4:
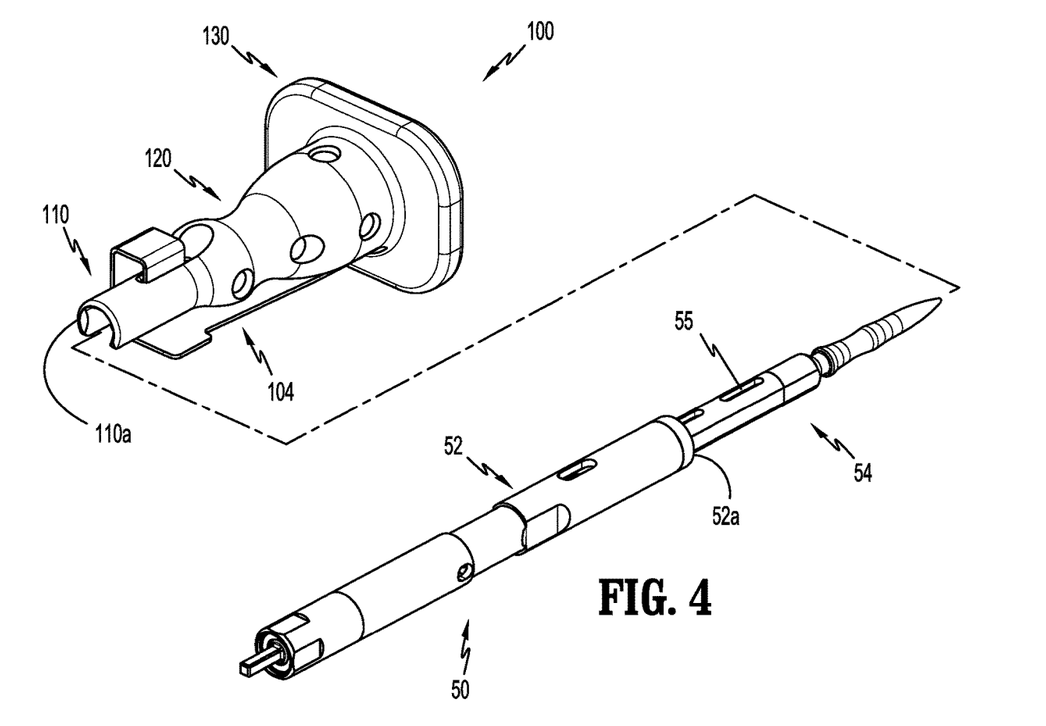
FIG. 4 is a side, perspective view of the trocar loading device shown in FIG. 3 and the removable trocar assembly shown in FIG. 2.

FIG. 3 illustrates a device for holding and aligning the removable trocar assembly 50 (FIG. 2) with the adapter assembly 20 according aspects of the disclosure is shown generally as trocar loading device 100. The trocar loading device 100 includes a base member 102 and an engagement arm 104 secured to the base member 102 by a screw 106. The base member 102 is configured to receive a proximal portion of the removable trocar assembly 50 (FIG. 2) and to align the removable trocar assembly 50 with the distal portion 24 (FIG. 2) of the adapter assembly 20, as described below. The engagement arm 104 of the trocar loading device 100 is configured to align the removable trocar assembly 50 with the base member 102 of the trocar loading device 100 and to releasably secure the removable trocar assembly 50 with the base member 102.

The base member 102 of the trocar loading device 100 includes a connector portion 110, a receiving portion 120 extending from the connector portion 110, and a handle portion 130 disposed on a free end of the receiving portion 120. The connector portion 110 is configured to facilitate engagement of the trocar loading device 100 with the adapter assembly 20. The receiving portion 120 is configured to receive the removable trocar assembly 50. The handle portion 130 is configured for operable engagement by a user. Although shown as being integrally formed, any or all of the connector portion 110, the receiving portion 120, and the handle portion 130 may be formed as separate components that are secured together using known methods.

The connector portion 110 of the base member 102 of the trocar loading device 100 is configured to be received within the connection member 26 (FIG. 8) of the distal portion 24 of the adapter assembly 20. The connector portion 110 may include an alignment feature (not shown) that is received within a slot 27 (FIG. 2) in the connector member 26 of the adapter assembly 20 to align the trocar loading device 100 with the adapter assembly 20. As will be described in further detail below, a proximal end surface 110a of the connector portion 110 of the base member 102 of the trocar loading device 100 is configured to engage a distal end surface 52a of the housing 52 of the removable trocar assembly 50 during attachment of the removable trocar assembly 50 to the adapter assembly 20 when the removable trocar assembly 50 is not properly secured within the adapter assembly 20.

The receiving portion 120 of the base member 102 of the trocar loading device 100 includes an elongate body 122 having a contoured section 124 and a tapered section 126. The contoured section 124 of the elongate body 122 is configured to facilitate engagement by a user of the trocar loading device 100 when separating the trocar loading device 100 from the removable trocar assembly 50 subsequent to the removable trocar assembly 50 being secured to the adapter assembly 20 (FIG. 2). As described below, the tapered section 126 of the elongate body 122 accommodates flexing of the engagement arm 104 of the trocar loading device 100 during attachment to and separation of the removable trocar assembly 50 from the trocar loading device 100.

The elongate body 122 of the base member 102 defines a longitudinal passage 121 configured to receive the trocar member 54 of the removable trocar assembly 50. An open distal end of the elongate body 122 facilitates cleansing and sterilization of the removable trocar assembly 50 while secured to the trocar loading device 100. The elongate body 122 of the base member 102 defines a slot 123 (FIG. 5) for receiving a locking portion 144 of the engagement arm 104. In aspects of the disclosure, and as shown, the elongate body 122 of the base member 102 defines a threaded opening 125 for receiving the screw 106 for securing the engagement arm 104 to the base member 102. The elongate body 122 may include flush ports 127 for permitting cleansing and sterilization of the removable trocar assembly 50 while the trocar loading device 100 is secured to the removable trocar assembly 50.

The handle portion 130 of the base member 102 of the trocar loading device 100 includes a substantially planar body 132 that extends radially outward from the receiving portion 120 of the base member 102. The planar body 132 of the base member 102 enables the trocar loading device 100, with the removable trocar assembly 20 secured thereto, to be maintained in an upright, standing position to accommodate placement of the removable trocar assembly 50 during handling and prior to assembly with the adapter assembly 20, without risk of contaminating and/or compromising the sterility of the removable trocar assembly 50.

The engagement arm 104 of the trocar loading device 100 includes an elongate portion 140, a release portion 142 formed on a free end of the elongate portion 140, a C-shaped flange portion 144 extending laterally from the release portion 142, and the locking portion 146 disposed on the flange portion 142 and extending towards the release portion 142. The engagement arm 104 may be integrally formed from a single piece of material. In aspects of the disclosure, the engagement arm 104 is formed of stamped sheet metal or molded plastic.

As shown, the engagement arm 104 of the trocar loading device 100 is secured to the base member 102 by the screw 106 received through an opening 141 formed in a second end of the elongate portion 140 of the engagement arm 104. The engagement arm 104 of the trocar loading device 100 is configured such that when the elongate portion 140 of the engagement arm 140 is secured to the base member 102 of the trocar loading device 100, the locking portion 146 of the engagement arm 104 is received within the slot 123 of the base member 102. The tapered section 126 of the base member 102 permits flexing of the engagement arm 104 to move the locking portion 146 of the engagement arm 104, as indicated by arrow "A" in FIG. 8, out of the slot 123 in the base member 102.

The locking portion 146 of the engagement arm 104 includes an inclined surface 146a to facilitate receipt of the removable trocar assembly 50 within the receiving portion 120 of the base member 102. More particularly, the inclined surface 146a of the locking portion 146 of the engagement arm 104 of the trocar loading device 100 engages the trocar member 54 of the removable trocar assembly 50 as the proximal end 54a of the trocar member 54 of the removable trocar assembly 50 is received with the longitudinal passage 121 of the base member 102 of the trocar loading device 100 to cause flexing of the engagement arm 104. In this manner, the locking portion 144 of the engagement arm 104 is moved from within the slot 123 in the base member 102 of the trocar loading device 100 to permit receipt of the removable trocar assembly 50 within the base member 102 of the trocar loading device 100.

The removable trocar assembly 50 is secured to the trocar loading device 100 by receiving the trocar member 54 in the longitudinal passage 121 of the base member 102 and aligning the slot 55 in the trocar member 54 with the cutout 125 in the base member 102 to permit receipt of the locking portion 146 of the engagement arm 104 into the slot 55 in the trocar member 54. The trocar member 54 of the removable trocar assembly 50 may have to be advanced from the trocar housing 52 in the event the removable trocar assembly 50 is provided with the trocar member 54 in a retracted position (not shown). As the removable trocar assembly 50 is received within the longitudinal passage 121 of the base member 102 of the trocar loading device 100, the inclined surface 146a of the locking portion 146 of the engagement arm 104 engages the trocar member 54 to cause the engagement arm 104 to flex to permit receipt of the trocar member 54 of the removable trocar assembly 50 within the base member 102 of the trocar loading device 100. Once the slot 55 in the trocar member 54 is aligned with the locking portion 146 of the engagement arm 104, the engagement arm 104 returns to its unflexed position and the locking portion 146 is received through the slot 123 in the base member 102 and through the slot 55 in the trocar member 54 to secure the removable trocar assembly 50 within the longitudinal passage 121 of the base member 102.

Once the trocar loading device 100 is secured to the removable trocar assembly 50, the trocar loading device 100 may be used to position the removable trocar assembly 50 within the adapter assembly 20. The removable trocar assembly 20 is secured to the adapter assembly 20 by receiving the connector portion 110 of the base member 102 of the trocar loading device 100 within the connector member 26 of the adapter assembly 20. Proper engagement of the removable trocar assembly 50 with the adapter assembly 20 may be indicated by an audible and/or tactile feedback.

In the noisy and active environment of an operating room, the feedback generated when the removable trocar assembly 50 is properly secured to the adapter assembly 20 may not always be heard and/or felt. The trocar loading device 100 is configured to permit confirmation that the removable trocar assembly 50 is properly secured to the adapter assembly 100 before separating the trocar loading device 100 from the removable trocar assembly 50. More particularly, the trocar loading device 100 is configured to register a strain in the strain gage assembly 28 (FIG. 2) of the adapter assembly 20 during retraction of the trocar member 54 of the removable trocar assembly 50 while the trocar loading device 100 is secured to removable trocar assembly 50 when the removable trocar assembly 50 is properly secured to the adapter assembly 20. Conversely, no strain is registered in the strain gage assembly 28 during retraction of the trocar member 54 when the removable trocar assembly 50 is not properly secured to the adapter assembly 20.

Figure 8:
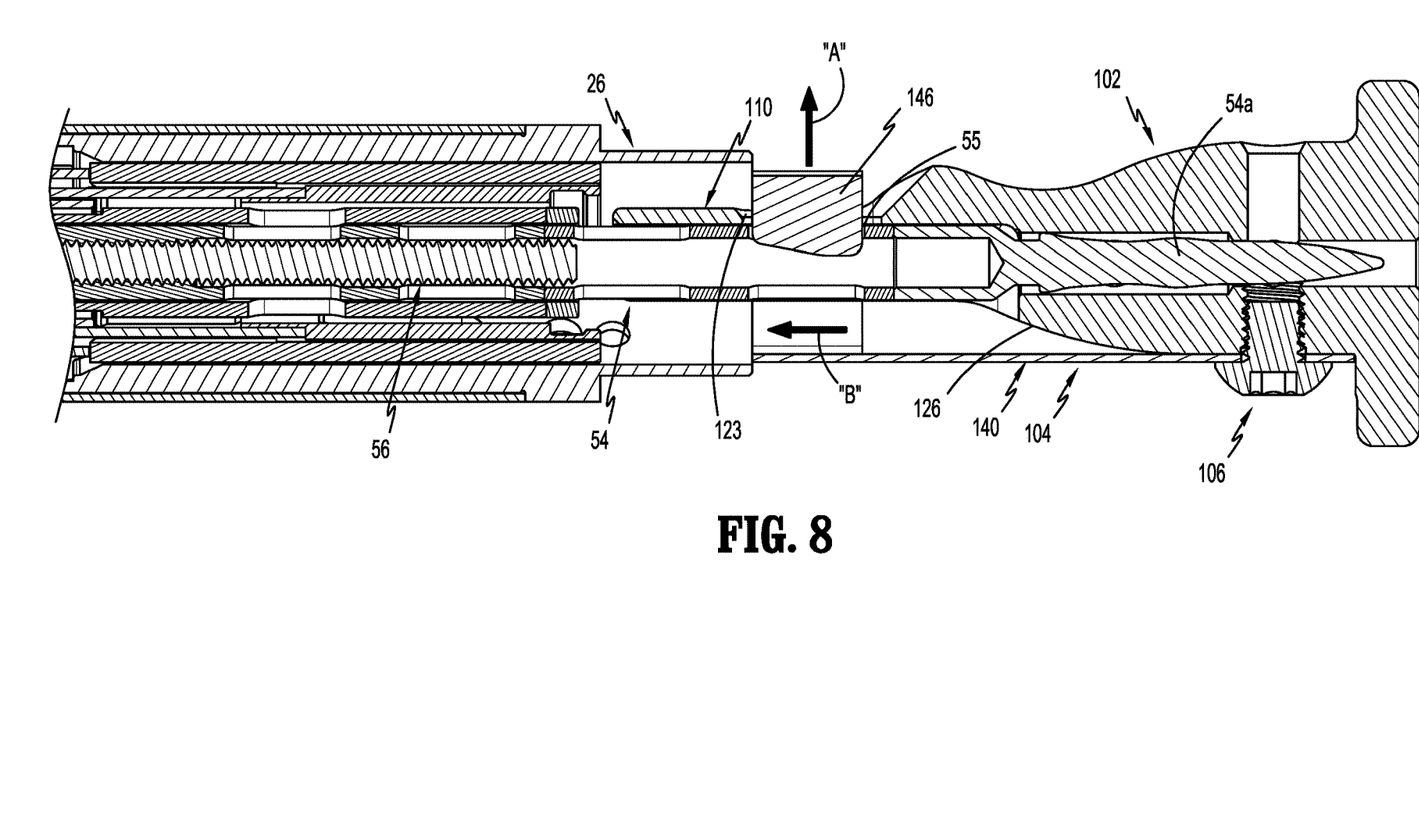
FIG. 8 is a cross-sectional side view of the adapter assembly, removable trocar assembly, and the trocar loading device as shown in FIG. 7, taken along line 8-8 shown in FIG. 7, with the removable trocar assembly properly engaged with the adapter assembly.

FIG. 8 illustrates the removable trocar assembly 50, including the trocar loading device 100 secured thereto, when the removable trocar assembly 50 is properly secured with the adapter assembly 20. When the removable trocar assembly 50 is properly secured with the adapter assembly 20, retraction of the trocar member 54 of the removable trocar assembly 50 relative to the trocar housing 52 of the removable trocar assembly 50, as indicated by arrow "B", causes a proximal surface 142a of the flange portion 142 of the engagement arm 104 to engage a distal surface 26a of the connector member 26 of the adapter assembly 20 prior to the proximal end surface 110a of the connector portion 110 of the base member 102 of the trocar loading device 100 engaging the distal end surface 52a of the trocar housing 52 of the removable trocar assembly 50. Engagement of the engagement arm 104 of the trocar loading device 100 with the connector housing 26 induces a load in the strain gage assembly 28 (FIG. 2) disposed within the adapter assembly 20, thereby indicating to the user that the removable trocar assembly 50 is properly engaged with the adapter assembly 20.

Figure 9:
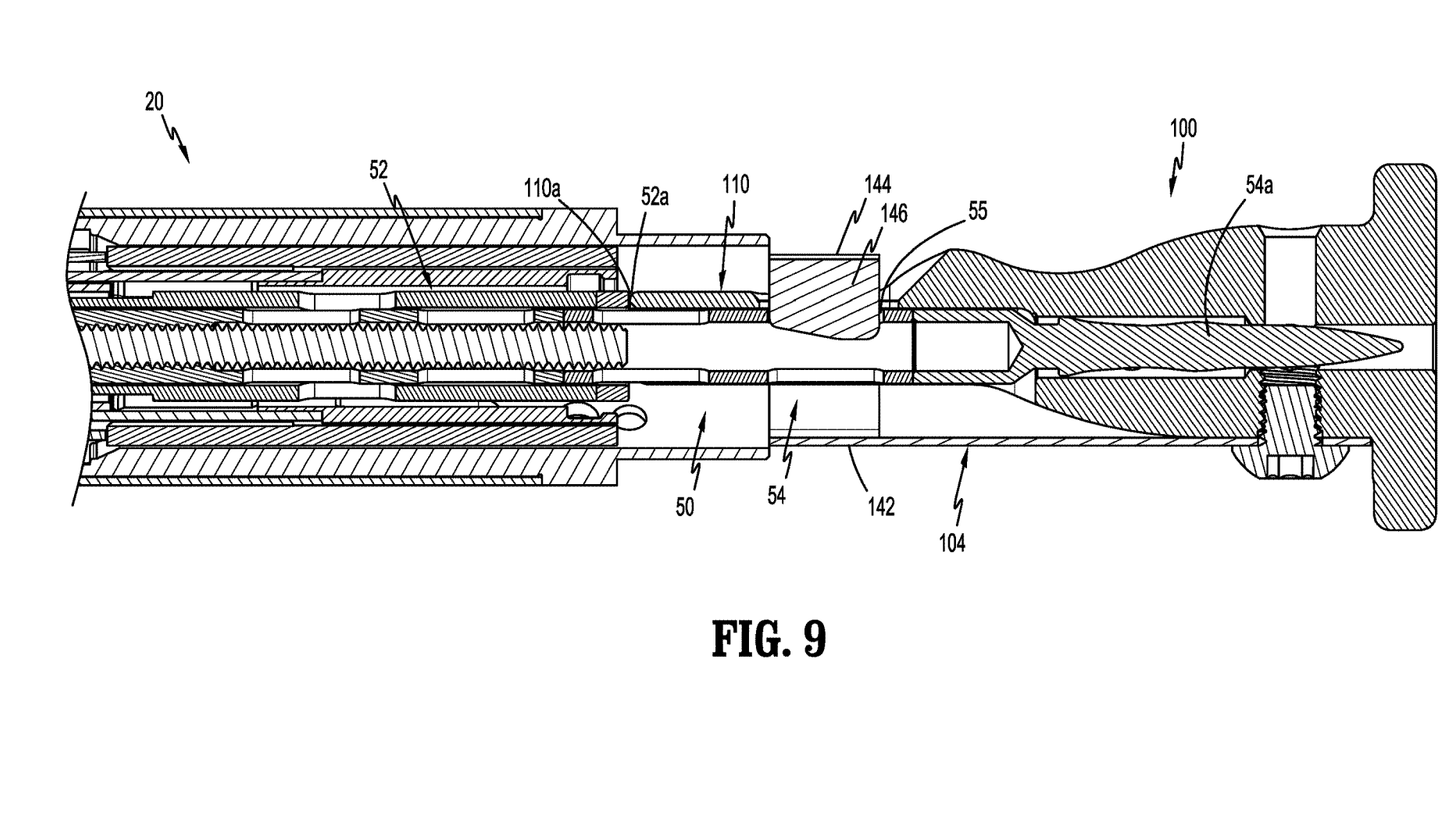
FIG. 9 is a cross-sectional side view of the adapter assembly, removable trocar assembly, and the trocar loading device as shown in FIG. 7, taken along line 8-8 shown in FIG. 7, with the removable trocar assembly not properly engaged with the adapter assembly.

FIG. 9 illustrates the removable trocar assembly 50, including the trocar loading device 100 secured thereto, when the removable trocar assembly 50 is not properly secured with the adapter assembly 20. When the removable trocar assembly 50 is not properly secured with the adapter assembly 20, retraction of the trocar member 54 of the removable trocar assembly 50 relative to the housing 52 of the removable trocar assembly 50 causes the proximal end surface 110a of the connector portion 110 of the base member 102 of the trocar loading device 100 to engage the distal end surface 52a of the trocar housing 52 of the removable trocar assembly 50 prior to the proximal surface 142a of the flange portion 142 of the engagement arm 104 engaging the distal end surface 26a of the connector member 26 of the adapter assembly 20, and thereby, preventing the engagement arm 104 of the trocar loading device 100 from engaging the connector member 26 of the adapter assembly. Since the engagement arm 104 of the trocar loading device 100 is prevented from engaging the connector housing 26, the strain gage assembly 28 (FIG. 2) disposed within the adapter assembly 20 does not register a load, thereby indicating to the user that the removable trocar assembly 50 is not properly engaged with the adapter assembly 20.

The handle assembly 30 of the surgical stapling instrument 10 may include a light and/or produce an audible sound when the strain gage assembly 28 registers a load. In addition, or alternatively, the handle assembly 30 may be configured to disable firing of the surgical stapling instrument 10 until a load is registered in the strain gage 28.

Once the removable trocar assembly 50 is properly secured with the adapter assembly 20, the trocar loading device 100 is separated from the adapter assembly 20 and the removable trocar assembly 50 by first flexing the engagement arm 104 by engaging the release portion 142 to move the locking portion 146 of the engagement arm 104 from within the slot 55 in the trocar member 54 of the removable trocar assembly 50 and then sliding the trocar loading device 100 longitudinally away from the adapter assembly 20 and from about the trocar member 54 of the removable trocar assembly 50.

After securing the removable trocar assembly 50 within the adapter assembly 20, operation of the adapter assembly 20 is substantially similar to operation of the exemplary adapter assemblies shown and described in the '879 publication, previously incorporated by reference herein in its entirety.

Persons skilled in the art will understand that the devices and methods specifically described herein and illustrated in the accompanying drawings are non-limiting exemplary aspects. It is envisioned that the elements and features illustrated or described in connection with the exemplary aspects may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. A trocar loading device for loading a trocar assembly within an adapter assembly, the trocar loading device comprising:
 a base member defining a longitudinal passage for receiving a trocar assembly and including a proximal end surface; and
 an engagement arm secured to the base member and configured to releasably secure a trocar assembly within the base member, the engagement arm including a proximal end surface, wherein the proximal end surface of the base member is configured to engage a distal end surface of a trocar housing of the trocar assembly only when the trocar assembly is not properly secured within the adapter assembly.

2. The trocar loading device of claim 1, wherein the proximal end surface of the engagement arm is configured to engage a distal end surface of a connection member of the adapter assembly when the trocar assembly is properly secured within the adapter assembly.

3. The trocar loading device of claim 2, wherein the base member includes a connector portion configured to be received within the connection member of the adapter assembly.

4. The trocar loading device of claim 1, wherein the base member includes a handle portion configured for operable engagement by a user.

5. The trocar loading device of claim 1, wherein the engagement arm includes an elongate portion, a C-shaped flange portion disposed on a first end of the elongate portion, and a locking portion extending from the flange portion.

6. The trocar loading device of claim 5, wherein the engagement arm further includes a release portion disposed adjacent the C-shaped flange portion and which is configured for operable engagement by a user.

7. The trocar loading device of claim 6, wherein the engagement arm is formed from a single piece of material.

8. The trocar loading device of claim 5, wherein the locking portion of the engagement arm includes an inclined surface to facilitate receipt of a trocar assembly within the base member.

9. The trocar loading device of claim 1, wherein the engagement arm is secured to the base member by the screw.

10. The trocar loading device of claim 1, wherein the base member includes a tapered section to accommodate flexing of the engagement arm.

11. A method of confirming proper securing of a removable trocar assembly within an adapter assembly, the method comprising:
 securing a trocar loading device to the removable trocar assembly;
 receiving proximal ends of the removable trocar assembly and the trocar loading device within the adapter assembly; and
 retracting a trocar member of the trocar assembly proximally until a proximal end surface of an engagement arm of the trocar loading device engages a distal end surface of a connection member of the adapter assembly or a proximal end surface of a base member of the trocar loading device engages a distal end surface of a trocar housing of the removable trocar assembly.

12. The method of claim 11, further including advancing the trocar member relative to the trocar housing to permit securing of the trocar loading unit to the removable trocar assembly.

13. The method of claim 11, wherein securing the trocar loading device to the removable trocar assembly includes receiving a locking portion of the engagement arm through a slot in the trocar member.

14. A trocar loading device for loading a trocar assembly within an adapter assembly, the trocar loading device comprising:
 a base member defining a longitudinal passage for receiving a trocar assembly and including a proximal end surface; and
 an engagement arm secured to the base member and configured to releasably secure a trocar assembly within the base member, the engagement arm including a proximal end surface, wherein the proximal end surface of the engagement arm is configured to engage a distal end surface of a connection member of the adapter assembly when the trocar assembly is properly secured within the adapter assembly and the proximal end surface of the base member is configured to engage a distal end surface of a trocar housing of the trocar assembly when the trocar assembly is not properly secured within the adapter assembly.

15. The trocar loading device of claim 14, wherein the base member includes a connector portion configured to be received within the connection member of the adapter assembly.

16. The trocar loading device of claim 14, wherein the base member includes a handle portion configured for operable engagement by a user.

17. The trocar loading device of claim 14, wherein the engagement arm includes an elongate portion, a C-shaped flange portion disposed on a first end of the elongate portion, and a locking portion extending from the flange portion.

18. The trocar loading device of claim 17, wherein the engagement arm further includes a release portion disposed adjacent the C-shaped flange portion and which is configured for operable engagement by a user.

19. The trocar loading device of claim 17, wherein the locking portion of the engagement arm includes an inclined surface to facilitate receipt of a trocar assembly within the base member.

20. The trocar loading device of claim 14, wherein the base member includes a tapered section to accommodate flexing of the engagement arm.

\* \* \* \* \*